Figure 1:
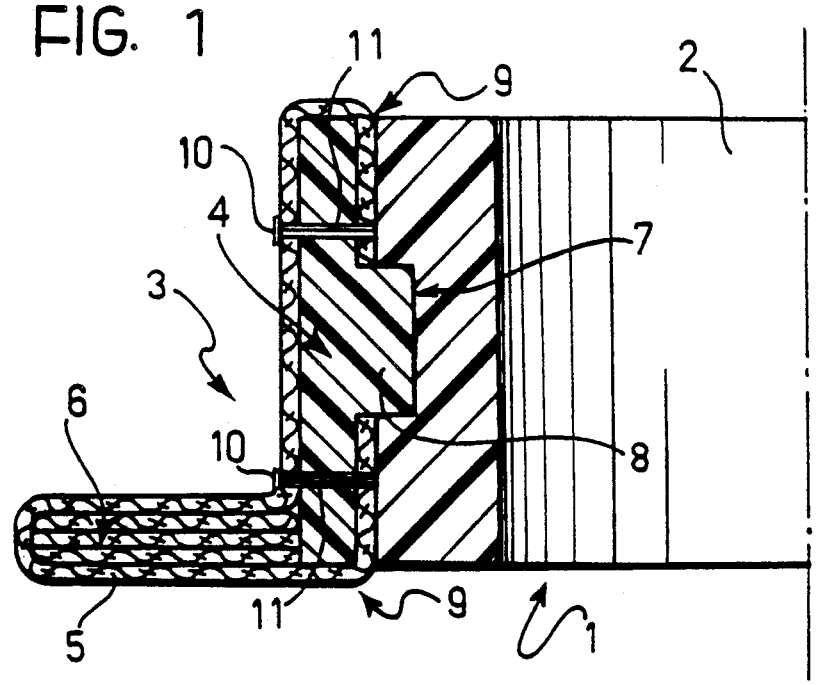

United States Patent [19]

Curcio et al.

[11] Patent Number: 5,104,406
[45] Date of Patent: Apr. 14, 1992

[54] HEART VALVE PROSTHESIS

[75] Inventors: Maria Curcio, Saluggia; Enrico Pasquino, Turin; Stefano Rinaldi, Parma; Franco Vallana, Turin, all of Italy

[73] Assignee: Sorin Biomedica S.p.A., Vercelli, Italy

[21] Appl. No.: 658,555

[22] Filed: Feb. 21, 1991

[30] Foreign Application Priority Data

Feb. 21, 1990 [IT] Italy .................. 67125 A/90

[51] Int. Cl.⁵ .................................................. A61F 2/24
[52] U.S. Cl. ............................................. 623/2; 623/900
[58] Field of Search ................................... 623/2, 900

[56] References Cited

U.S. PATENT DOCUMENTS

| | | | |
|---|---|---|---|
| 3,996,623 | 12/1976 | Kaster | 623/2 |
| 4,197,593 | 4/1980 | Kaster et al. | 623/2 |
| 4,535,483 | 8/1985 | Klawitter et al. | 623/2 |
| 4,778,461 | 10/1988 | Pietsch et al. | 623/2 |
| 4,863,460 | 9/1989 | Magladry | 623/2 |

FOREIGN PATENT DOCUMENTS 3507109 9/1986 Fed. Rep. of Germany ......... 623/2

Primary Examiner—Randall L. Green
Assistant Examiner—David H. Willse
Attorney, Agent, or Firm—Shea & Gould

[57] ABSTRACT

A heart valve prosthesis has a suture ring with a core for form-coupling with the stent of the prosthesis so that the suture ring and the stent are held securely together axially, while the core can rotate relative to the stent. The suture ring has a covering which cooperates with the surface of the stent and is in contact therewith. The degree of contact determines the resistance to relative rotation of the ring and the stent.

10 Claims, 1 Drawing Sheet

HEART VALVE PROSTHESIS

DESCRIPTION

The present invention relates to heart valve prostheses and more specifically to a prosthesis including a stent in which the obturator means of the prosthesis are mounted and a suture ring which is fitted around the stent.

Heart valve prostheses of the type specified above are widely known in the art.

In order to produce the suture ring of the prosthesis, that is, the generally flexible and soft annular element through which the suture stitches which fix the prosthesis firmly in its implant position are intended to extend, it is necessary, in all circumstances, to avoid the risk of the stent of the prosthesis being displaced axially as a result of any stress so that, in the worst cases, it comes out of the suture ring with disastrous consequences for the wearer of the prosthesis.

This requirement can be satisfied if the suture ring is fitted tightly around the stent of the prosthesis. This solution conflicts, however, with the need to enable the surgeon to orient the stent (and hence the obturator or obturators of the prosthesis) once the prosthesis is seated in its implant position so as to achieve the most favourable position from an anatomical point of view and as regards the blood flow.

There is thus a need to achieve a compromise in which the stent is held securely in the suture ring axially but can still be oriented easily and with little effort by the surgeon.

This characteristic is normally known in English technical terminology as "turnability". It can be measured in absolute terms by the measurement, by means of a torsion dynamometer, of the resistance to relative movement of the suture ring and the stent after the prosthesis has been placed on a support (a so-called holder) which is urged to rotate about the main axis of the prosthesis whilst the suture ring is restrained in a fixed position. In practice, however, most manufacturers prefer to use relative evaluation criteria.

It is commonly found that relative turnability values vary within a range of 1 to 3 for prostheses which are nominally identical.

This wide variability of the turnability, which is caused by various factors affecting the production of the prostheses cannot, however, be considered satisfactory.

There is thus a need to provide heart valve prostheses in which the suture ring and the stent can be coupled with precisely predetermined relative rotation (turnability) characteristics which are repeatable on a large scale without appreciable variation.

According to the present invention, this object is achieved by virtue of a heart valve prosthesis having the characteristics recited specifically in the claims which follow.

Figure 2:
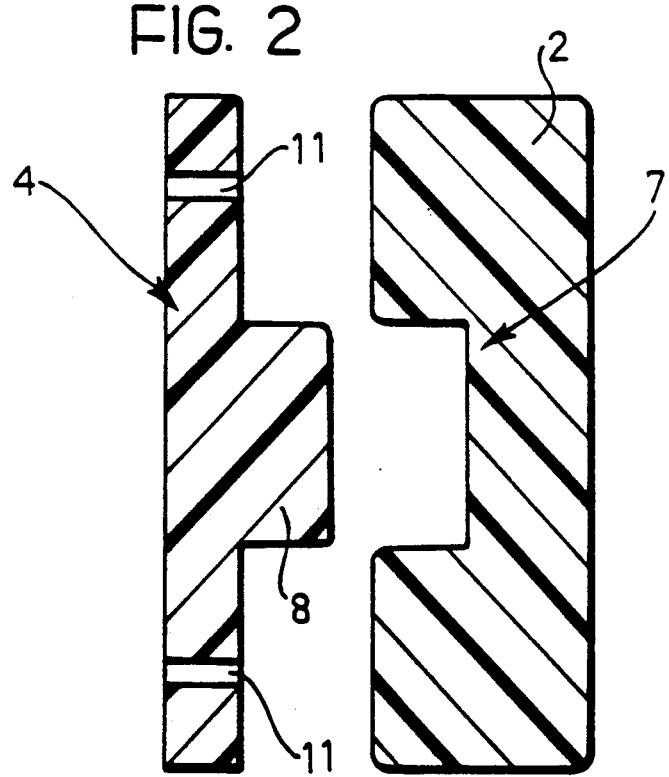

The invention will now be described, purely by way of non-limiting example, with reference to the appended drawings, in which:

FIG. 1 is a partial section showing the structure of a heart valve prosthesis according to the invention, and FIG. 2 shows, in greater detail, the relative dimensional characteristics of some parts shown in FIG. 1.

In FIG. 1, a heart valve prosthesis (not shown as a whole) is generally indicated 1. This is a valve prosthesis of the type including an annular stent or housing 2 of substantially rigid material (for example, titanium, stellite, etc.) within which one or more pivoting obturators or prosthetic valve flaps are mounted for pivoting between a generally closed position (in which the blood flow is obstructed) and a generally open position (in which the blood flow is unobstructed).

The obturator means are not shown specifically in the drawings since their structure and characteristics are not relevant for the purposes of an understanding of the present invention.

By way of reference, it should be pointed out that the solution according to the invention has been developed with particular attention to its possible use in the field of mechanical heart valve prostheses with pivoting obturators.

Another generally flexible, soft annular element 3 is disposed around the stent 2 and constitutes the so-called suture ring which is intended to be sutured to the surrounding tissue so as to ensure that the prosthesis is held securely in its implant position after the natural valve flaps have been removed.

Essentially, the suture ring 3 is constituted by a core 4 of generally T- or omega-shaped cross-section surrounded by a covering of biocompatible synthetic fabric.

The outer covering 5 is preferably made of two different materials according to the criteria described in greater detail in commonly assigned U.S. patent application Ser. No. 07/658,535 filed Feb. 21, 1991.

In particular, the covering 5 forms, on the outer surface of the suture ring 3, a padded loop 6 through which the surgical stitches used to fix the prosthesis in its implant position are intended to pass.

The main characteristic of the prosthesis according to the invention is the particular manner in which the suture ring 3 is coupled to the stent 2.

The stent has an annular groove 7 in its external surface in an approximately central position between its axially opposite ends, forming a seat for housing an internal radial appendage 8, which is also annular, of the core 4 of the suture ring.

As can be appreciated better from the detailed drawing of FIG. 2, the relative dimensions of the groove 7 and the annular appendage 8, as well as the relative diameters of the external surface of the stent 2 and the internal surface of the core 4, are determined in such a way that the core 4 is held securely on the stent 2 as regards axial relative movements (so that the stent 2 is prevented from coming out of the suture ring 3 in all circumstances) whilst the core 4 can rotate easily around the stent 2.

By way of reference, if one considers a stent 2 about 8 mm high and with a maximum outside diameter of 27.8 mm, the groove 7 is formed with a width (measured axially of the stent 2 itself) of the order of 2 mm and a depth of 0.4 mm.

The core 4 of the suture ring, however, has an inside diameter of the order of 28.8 mm. The width of the annular appendage 8 is 1.9 mm and its depth or height is 0.85 mm.

The stent 2 is usually made of a substantially rigid material such as titanium; the core 4 of the suture ring, however, is made of a generally resilient material such as the paraformaldehyde polymer currently known by the trade name of Delrin. The resilience of the core 4 (and in particular its radial extensibility) enable the suture ring 3 to be fitted around the stent 2 by being expanded radially and then fitted onto the stent 2 until the ring 3 can contract again as a result of the snap-engagement of the annular appendage 8 in the groove 7.

The suture ring is fitted (after the covering 5 has been applied to the core 4) by being expanded mechanically (by means of an expander) and then moved to the desired position of axial alignment (with the appendage 8 facing the groove 7), the expander then being removed. Generally, the mechanical characteristics of the material constituting the core 4 are such that, once it has reached the position in which it is fitted firmly onto the stent 2, the core 4 cannot be removed from the stent 2 again except by great force. This is due mainly to the secure restraint of the annular appendage 8 within the groove 7. As seen above, however, the coupling of the appendage 8 in the groove 7 is not such as to cause much restraint or interference as regards relative rotation; in other words, the core 4 alone (that is, without the covering 5) can easily be rotated about the stent 2.

As can better be seen in FIG. 1, the covering 5 does not cover the core 4 completely. In fact, it leaves the annular appendage 8 uncovered and is inserted only in the annular spaces 9 defined jointly by the opposite cylindrical surfaces of the internal face of the core 4 and of the external face of the stent 2 in the axial regions flanking the central region in which the groove 7 and the annular appendage 8 extend. These annular spaces are, for example, of the order of 0.4 mm wide (measured radially of the general extent of the prosthesis 1).

The parts of the covering 5 inserted in these spaces and sewn to the core 4 of the suture ring 3 by stitches 10 extending through corresponding holes 11 in the core cooperate with the external surface of the stent 2 and are in contact therewith.

They therefore act, so to speak, as a friction material whose characteristics of thickness, resilience, surface finish, smoothness of the constituent material, etc., that is, the characteristics of their contact with the outer surface of the stent 2, define the characteristics of the resistance to the relative rotation of the suture ring 3 and the stent 2 univocally and in a manner which can be repeated on a large scale without wide variations.

With reference to the dimensional example given above, in which the annular spaces 9 are of the order of 0.4 mm wide radially, the parts of the covering 5 which are inserted therein may be made of a material woven from a synthetic polytetrafluoroethylene (Teflon) and/or polyethylene terephthalate (Dacron) yarn with an apparent thickness (in fact, one is speaking about woven materials which may have a surface with a pile) of the order of 0.4-0.5 mm, that is, slightly greater than the radial widths of the spaces 9.

The Applicant has found that, with this choice of dimensions, heart valve prostheses can be produced regularly with turnability values which, with reference to the evaluation values referred to above, fall between 1.5 and 2, and hence with a much more restricted and concentrated distribution of turnability values than was found previously, without the need to discard prostheses the turnability values of which are too high.

Naturally, the dimensions of the annular spaces 9 may even vary quite widely if the materials used for the covering 5 have different thicknesses, dimensions and structures from those referred to above.

The variation of the dimensional parameters in dependence on the different characteristics of the materials constitutes a simple design variant within the scope of the general principle of the invention and should therefore be considered to fall within the scope of the present patent.

Naturally, the foregoing also applies to different configurations of the valve prosthesis. The embodiment illustrated in the drawings in fact relates specifically to a mitral valve prosthesis. The invention can be applied directly to a different type of valve prosthesis (for example, an aortic prosthesis) without requiring any substantial modification of the embodiment described above.

Consequently, the principle of the invention remaining the same, the details of construction and forms of embodiment may be varied widely with respect to those described and illustrated, without thereby departing from the scope of the present invention.

What is claimed is:

1. A heart valve prosthesis comprising a stent, obturator means mounted in the stent, and a suture ring which is fitted around the stent, wherein the suture ring has a core with means which engage the stent and can hold the ring and the stent together axially whilst enabling the core of the ring to rotate relative to the stent, and a covering is applied to the core by directly stitching the covering to the core, at least part of said covering being intended to cooperate with the surface of the stent and to be in contact therewith, the degree of contact determining the resistance to relative rotation of the ring and the stent, and wherein the engagement means of the stent is left completely uncovered by the covering.

2. A prosthesis according to claim 1, wherein the engagement means comprises an annular appendage projecting from an internal surface of the core of the suture ring and the stent has an external groove forming a seat for housing at least part of the annular appendage.

3. A prosthesis according to claim 2, wherein the width and depth of the annular groove are greater than the corresponding dimensions of at least the said part of the annular appendage.

4. A prosthesis according to claim 1, wherein the stent is made of a substantially rigid material and the core is made of a resiliently deformable material whereby the suture ring can be mounted on the stent by radial expansion of the suture ring.

5. A prosthesis according to claim 4, wherein the core fits the stent with slight interference so as to contribute to the resistance to relative rotation of the ring and stent.

6. A prosthesis according to claim 1, wherein the core and the stent together define at least one annular space in which the covering is inserted in order to contact the surface of the stent.

7. A prosthesis according to claim 6, wherein the core and the stent form at least two annular spaces at axially opposite ends of the prosthesis.

8. A prosthesis according to claim 1, wherein the core has a generally T- or omega-shaped cross-section.

9. A prosthesis according to claim 1 wherein the core fits the stent with slight interference so as to contribute to the resistance to relative rotation of the ring and the stent.

10. A prosthesis according to claim 9, wherein the slight interference is achieved by virtue of the resilience of the material constituting at least one of the core and the stent.

* * * * *